United States Patent [19]

Pare et al.

[11] Patent Number: 5,214,287
[45] Date of Patent: May 25, 1993

[54] SYSTEM FOR INSTALLING A COLLIMATOR IN A GAMMA CAMERA

[75] Inventors: Christian Pare, Plaisir; Christophe Fleury, Antony, both of France

[73] Assignee: Sopha Medical, Paris, France

[21] Appl. No.: 687,895

[22] PCT Filed: Nov. 30, 1989

[86] PCT No.: PCT/FR89/00620
§ 371 Date: Jun. 7, 1991
§ 102(e) Date: Jun. 7, 1991

[87] PCT Pub. No.: WO90/06083
PCT Pub. Date: Jun. 14, 1990

[30] Foreign Application Priority Data
Dec. 7, 1988 [FR] France .................. 88 16069

[51] Int. Cl.[5] .................. G01T 1/164; A61B 6/00
[52] U.S. Cl. .................. 250/363.1; 378/147
[58] Field of Search ............. 250/363.10; 378/147

[56] References Cited
U.S. PATENT DOCUMENTS
3,982,133  9/1976  Jupa et al. ................. 250/363.1
4,629,893  12/1986  Hanz et al. ................. 250/363.1

FOREIGN PATENT DOCUMENTS
0156112  10/1985  European Pat. Off. .
0194728   9/1986  European Pat. Off. .
59090073  5/1984  Japan .
60-165568 8/1985  Japan .
0293179  12/1987  Japan ................. 250/363.10

*Primary Examiner*—Janice A. Howell
*Assistant Examiner*—Richard Hanig
*Attorney, Agent, or Firm*—Oblon, Spivak, McClelland, Maier & Neustadt

[57] ABSTRACT

The system includes a frame provided with jaws (8, 9) for grasping the collimator. The collimator and the case include a system of retractable studs that co-operate with reaction members to retain the collimator (2) on the case (5). The jaws act on the studs (46) to detach the collimator from the case while simultaneously grasping the collimator. It is shown that by acting in this way, the collimator is permanently retained and simultaneously collimator installation and fixing operations are facilitated.

9 Claims, 2 Drawing Sheets

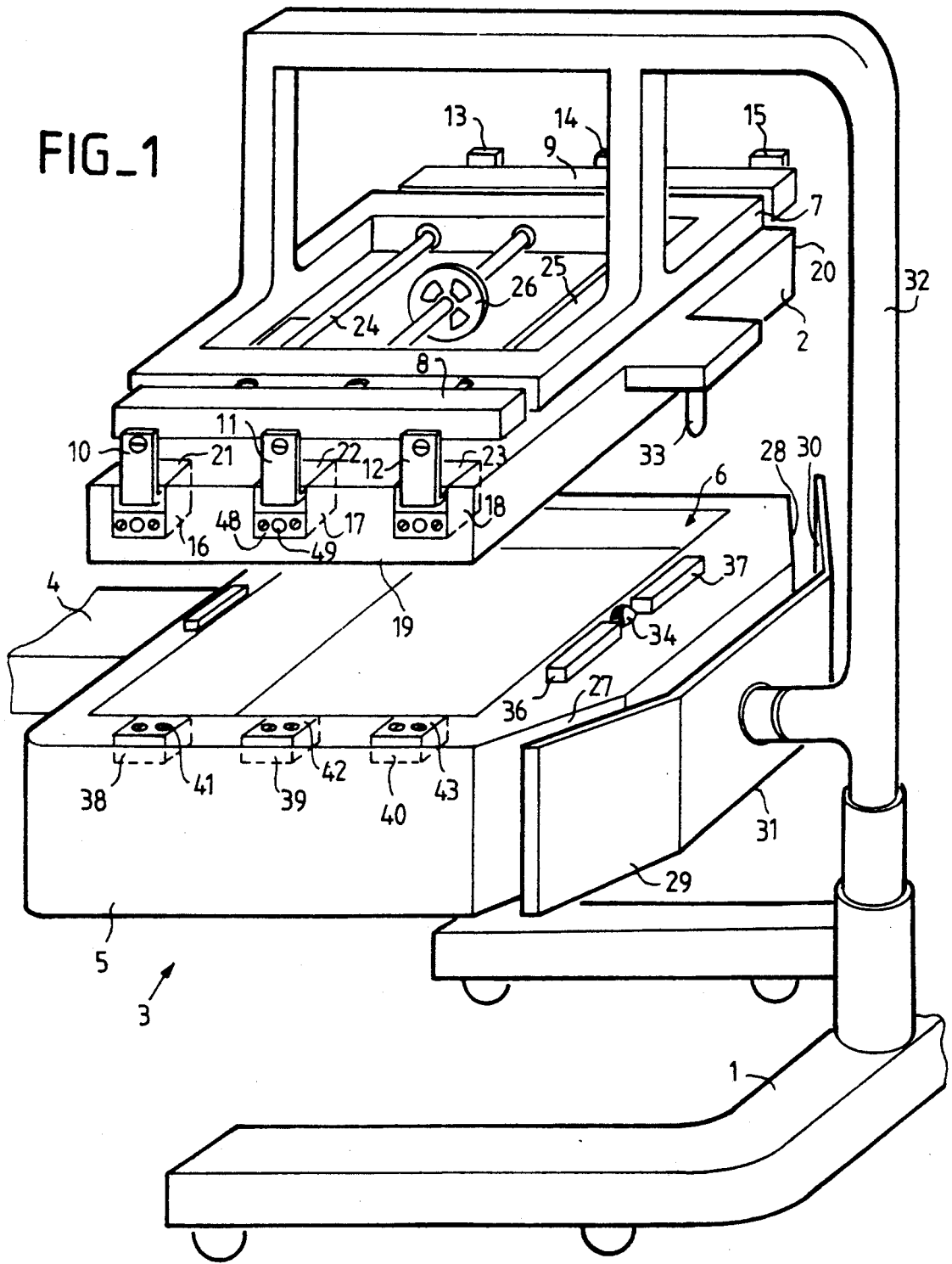
FIG_1

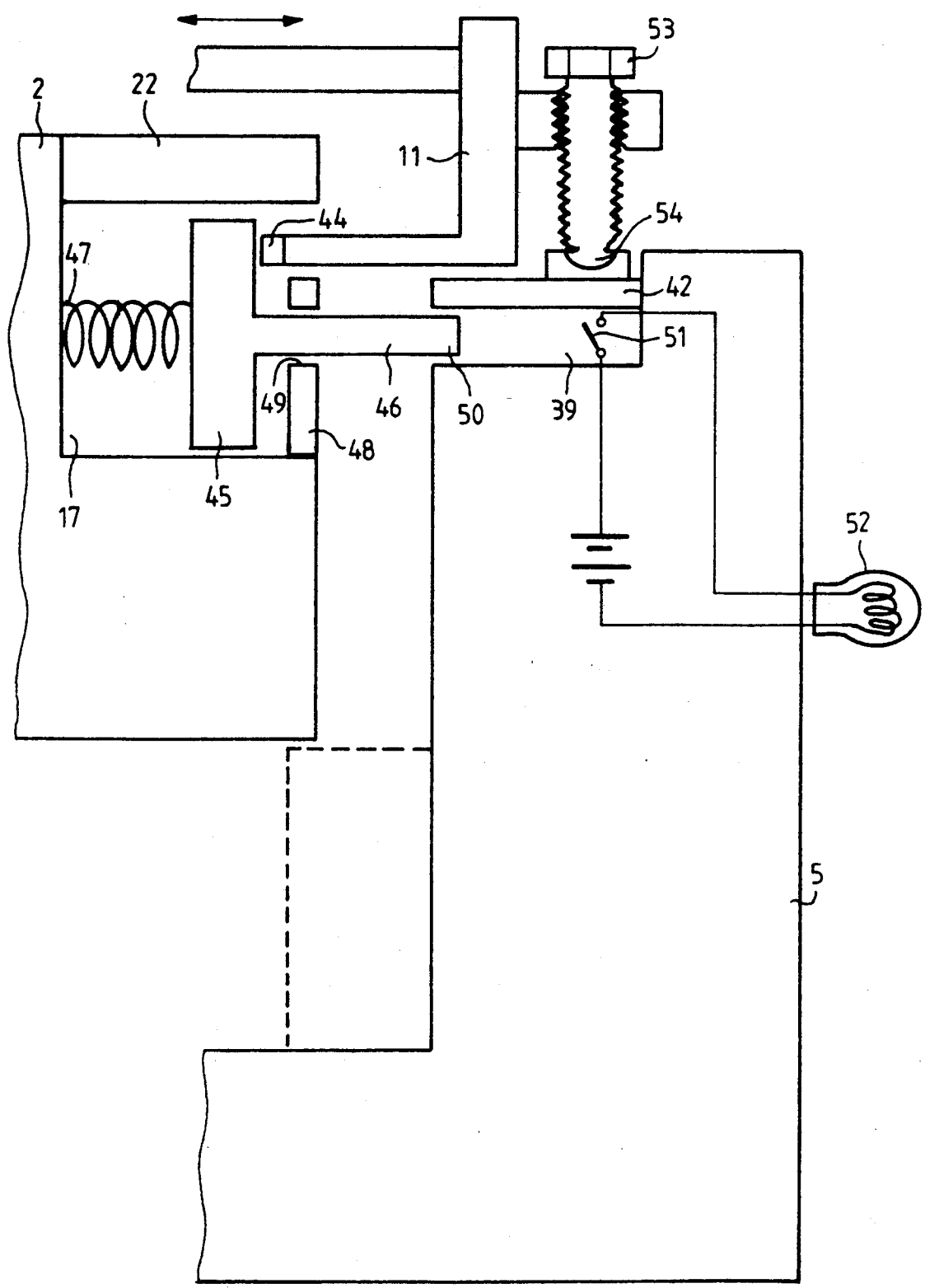
FIG_2

SYSTEM FOR INSTALLING A COLLIMATOR IN A GAMMA CAMERA

BACKGROUND OF THE INVENTION

1. Field of the Invention

The invention relates to a system for installing a collimator in a gamma camera. It is intended for use particularly in medical imaging. A gamma camera is an assembly of equipment: detector, stand, and console, enabling nuclear medicine examination to be performed. The collimator of a gamma camera is fixed to the detector.

2. Discussion of the Background

A gamma camera is conventionally used as follows. Patients subjected to examination on such apparatus have a tracer containing a radioactive isotope injected into their bodies. The isotope fixes itself preferentially in a particular organ depending on the type of tracer injected. The function of the gamma camera is to form the image of the plane projection of the gamma radioactivity fixed by said organ, thus revealing its functional state. The image is obtained by detecting gamma radiation coming from the organ under examination and emitted in a single direction so as to project the concentration of the isotope in the organ in said direction. A gamma camera thus comprises a gamma radiation detector constituted, in particular, by a large-area scintillator crystal covered with a network of photomultipliers. When a gamma ray passes through the scintillator, it produces local scintillation which is detected by a plurality of photomultiplier tubes situated in the vicinity of the scintillation. The photomultipliers provide electrical current proportional to the received scintillation. This makes it possible to locate the impact of gamma rays in the scintillator crystal by evaluating the center of gravity of the signals delivered by the photomultipliers.

A device called a "collimator" situated immediately in front of and against the detector is used to select for detection only those gamma rays that are emitted in a single direction, e.g. a direction perpendicular to the inlet face of the scintillator.

In outline, a collimator is an absorbent plate, generally made of lead, which is pierced by a multitude of ducts that pass gamma rays only over a very small solid angle whose axis is parallel to the desired projection direction for the image of radioactive isotope distribution that is to be produced.

In practice, collimators are designed as a function of the energy of the gamma radiation emitted by the isotope injected into the patient and as a function of the desired transparency and spatial resolution characteristics that are to be obtained. In general terms, spatial resolution and transparency depend on the size of the solid angle of the collimator ducts, and it is clear that these two characteristics vary in opposite directions. Depending on the types of examination performed using nuclear medicine, use is made of substances that emit gamma rays at different energies, or else specific resolution and transparency characteristics are required for the collimators. Under such circumstances, a gamma camera is generally fitted with a family of collimators having different geometrical characteristics. In routine operation of the gamma camera, it must be possible to swap the collimator associated with the detector of the camera for a particular examination with another collimator at the request of the operator performing the examination.

The thickness, or in practice the weight, of the collimator depends on the energy of the radiation to be detected and on the looked-for solid angle characteristics. In addition, detectors are generally cantilevered out from a bracket. The unbalance due to the cantilevered detector is normally compensated by counterweights disposed in the mechanism for moving or handling the detector. Since it is not easy to change these counterweights, it has become the practice to associate peripheral masses with lightweight collimators (collimators for low-energy radiation), thereby ensuring that they weigh as much as heavier collimators. When the working weight of the collimators may lie in the range 20 kg to 60 kg, this technique consists in providing collimators which, together with their associated masses, always weigh about 60 kg.

Collimators of such a weight cannot be handled without mechanical equipment. In practice, the gamma camera detector is contained in a metal case in the form of a large pot provided with a rabbet or groove for receiving the collimator. The collimator constitutes a kind of lid for the detector and the case. Installation is based on the principle of lifting the collimator by applying force from below on the outside face of the collimator when said face is turned face-down. In such handling, the collimator is applied to the detector from below after previously turning over the detector. For example, two handling arms mounted on a carriage bear against said outside face from below and disengage the collimator from its storage position. The carriage is then displaced into the vicinity of the gamma camera. To install the collimator, given that the detector is upsidedown with the opening to its case at the bottom, its "lid" is applied thereto by raising the two handling arms. Since this operation is performed from below, it is performed blind.

The collimator is in the form of a relatively thick slab. With a round-field detector, the collimator is naturally round. Round collimators are fixed as follows. A circular groove is formed in the edge of the collimator plate and surrounds the plate. When the collimator is installed to close the case, this groove comes level with a system of screws fixed to the case. The tips of the screws are engaged into the groove by tightening the screws manually. Once the parts are engaged together, the carriage and its handling arms may be withdrawn.

Given that it must be possible for the gamma camera to be used at any angle in three dimensions, and in particular that it must be possible for it to be above the patient, operators responsible for installing collimators are in the habit of tightening the collimator fixing screws very firmly. This avoids any risk of the collimator becoming detached since it could seriously injure a patient by falling. This assembly technique suffers from three drawbacks. Firstly the system is unhandy since it has to be operated blind at the moment the collimator is installed. Given that installation takes place from below, the operator cannot see at exactly which moment the carriage is properly in place, and this makes it difficult to center the collimator relative to the opening in the case. Secondly, tightening the screws excessively can sometimes make it difficult to lossen them again when the collimator is to be replaced.

Further, the use of round sealed gamma cameras is presently being replaced by the use of gamma cameras in which the examination field is square or rectangular.

Under these conditions, centering becomes even more difficult since for mechanical reasons the collimator is also rectangular and needs to be inserted into a rectangular opening. This is difficult to do when acting blind and from below.

There exists a second solution which is also applicable to collimators for a round field gamma camera. In such cameras, the collimators possesses retractable handles that can be grasped by a sufficiently sturdy operator who then approaches the opening in the gamma camera case while it is upwardly directed. The operator then lowers the collimator at arms' length onto the opening and rotates it through a quarter turn to engage studs mounted on the edge of the collimator or on the case into bayonet fittings mounted on the corresponding portion of the case or the collimator. This method of fixing can naturally only be used for lightweight collimators, and because of the quarter turn, it is unfortunately usable only with round collimators.

A third technique exists in which a carriage engages a collimator by means of hooks and places the collimator onto a gamma camera case from above. Once the collimator has been placed on top of the case, screws are engaged through the collimator so as to be received in the solid portion of the case. The heads of the screws enable the collimator to be held in place when the gamma camera is turned over so that the outside face of the collimator faces the ground. The drawback presented by this technique relates largely to the need to tighten a large number of screws, thereby wasting operator time. In addition, as in the preceding cases, the screws may be overtightened out of concern for safety, such that subsequent loosening can become difficult.

In addition, there is another problem that arises: this is the problem of moving the collimator from the cupboard in which it is stored to the gamma camera that is to receive it while ensuring sufficient safety to prevent the collimator escaping from the manipulator arms of the carriage.

SUMMARY OF THE INVENTION

An object of the invention is to remedy all these drawbacks by providing a system for installing the collimator in which mechanical co-operation exists between the handling carriage, the collimator, and the case of the gamma camera. In particular, the unlocking of collimators from their locations in the storage cupboard is concomitant with the locking of the collimators on the moving carriage for transporting them. Similarly, they are unlocked from the moving carriage simultaneously with their being locked to the case of the gamma camera at the final position of use.

In other words, the invention ensures that collimators are locked at all times whenever they travel between the cupboard in which they are stored and the gamma camera on which they are used. The invention thus prevents any dangerous handling and any danger of said collimators falling while they are being handled. In addition, the invention naturally simplifies the operations of locking and unlocking collimators at their starting and destination positions as much as possible by semiautomatic interaction between the carriage and locking mechanisms existing in the cupboard and/or on the gamma camera case.

The invention thus provides a system of installing a collimator on a gamma camera detector, the system comprising a handling carriage, a collimator, and a gamma camera carried by a case, the system being characterized in that:

the carriage includes a frame provided with jaws for grasping the collimator;

the collimator and the case include a system of retractable studs and of reaction members co-operating with the studs to hold the collimator on the case; and the jaws co-operate with the studs to detach the collimator from the case while simultaneously grasping the collimator or to attach the collimator to the case while simultaneously releasing it from the carriage.

The invention will be better understood on reading the following description and on examining the accompanying figures. These figures are given merely by way of example and they do not limit the invention. In the figures:

BRIEF DESCRIPTION OF THE DRAWINGS

FIG. 1 is a diagram of the system of the invention at the moment when a collimator is being installed on the case; and FIG. 2 is a diagram in section through the system of the invention for mounting the collimator on a gamma camera.

DETAILED DESCRIPTION OF THE INVENTION

Although the description is provided with reference to mounting a collimator on a gamma camera, it will be understood that similar devices can be installed in the storage cupboard, thereby enabling the carriage to perform operations in the cupboard that are the inverse of the operations it performs on the collimator. The mounting operation is described, since the dismounting operation is simply derived therefrom by performing the same operations in the opposite order. FIG. 1 shows a carriage 1 suitable for bringing a collimator 2 up to a gamma camera 3. The carriage has castors running on the ground, with the gamma camera being cantilevered out from the end 4 of a bracket. The gamma camera 3 comprises a case 5 having a cavity 6 which is assumed to contain its scintillator and its photomultiplier tubes. The cavity 6 is to be closed by the collimator 2. The carriage 1 comprises a frame 7 provided with jaws 8 and 9. In the example shown, each jaw has three teeth with respective reference numerals 10 to 12 and 13 to 15. The teeth are L-shaped, each having an angled end for engaging in cavities such as 16 to 18 formed in the tooth-facing edges 19 and 20 of the collimator.

In order to enable the ends of the teeth 10 to 15 to engage the collimator, the tops of the cavities such as 16 to 18 are closed by plates such as 21 to 23 which are fixed by any suitable means, e.g. screws. The two jaws are connected to each other and to the frame by slides such as 24 and 25. These slides allow the jaws to move parallel to the plane of the frame 7. To perform this displacement, a quarter turn type operating handle 26 serves to move the jaws 8 and 9 symmetrically towards or away from respective facing side longitudinal members of the frame 7, depending on the direction in which the handle is rotated. The jaws are parallel to the length members. When the jaws are moved towards each other, the ends of the L-shapes of the teeth 10 to 15 engage beneath the plates 21 to 23 in the cavities such as 16 to 18 of the collimator 2. Under these conditions, the collimator is retained and it may be displaced across a medical examination room to bring it up to the gamma camera.

The invention is more particularly advantageous for use with rectangular type collimators, in which case the jaws 8 and 9 can be made from straight bars suitable for placing on opposite sides of two opposite edges of the rectangular collimator. To make installation easy and to facilitate centering of such a rectangular collimator, the case of the gamma camera is also provided with a tapering face having two sloping flats 27 and 28 for coming into abutment against respective end faces 29 and 30 of a shield 31 mounted on the carriage 1. The shield can be adjusted once and for all relative to the gamma camera with which it is associated so that collimator installation is immediate.

The frame 7 is supported by a bracket 32. The bracket 32 is preferably telescopic to enable the collimator 2 to be installed on the case 5 by being lowered and also to enable different collimators to be stored on different shelves in a single storage cupboard. Whereas the shield 31 provides coarse adjustment for collimator installation, a set of conical pegs such as the pegs 33 provide fine adjustment for collimator installation on engaging in cavities 34 designed to receive them and formed in the case 5. These cavities 34 are additionally surrounded by shoes such as 36 and 37 which serve firstly as wear parts and secondly as adjustable abutments for adjusting a machine as a function of its set of four or five collimators. Collimators are generally molded, and they do not always have exactly the same dimensions. It is general to accept tolerance of five-tenths of a millimeter.

Facing the locations having the cavities 16 to 18 in the collimator, when the collimator is installed on the case 5, there are further cavities such as cavities 38 to 40 respectively formed in the inside vertical edges of the case 5 or in a rabbet thereof. Each of these cavities 38 to 40 is covered with a respective reaction plate 41 to 43 which is fixed to the case 5 by any appropriate means, e.g. by screws.

FIG. 2 is a section in section plane C of FIG. 1 through the system for engaging and disengaging the teeth of the jaws in the cavities 16 to 18. In this figure, it can be seen that the tooth 11 is capable of moving horizontally to enter or leave the cavity 17. The top of the cavity 17 is closed by the reaction plate 22 which enables the tooth 11 to grasp the collimator 2. On being inserted, the end 44 of the tooth 11 bears against a base 45 of a stud 46. The stud is in the form of a round rod and is normally pushed outwards from the cavity 17 by means of a spring 47 which acts between the end of the cavity and the back of the base 45. The stud 46 is prevented from leaving the cavity 17 when the tooth 11 is withdrawn by the presence of a closure plate 48 provided with a hole 49. The hole allows the rod of the stud to pass. For the cavity 17, these details are also visible in FIG. 1.

During transport, the tooth 11 is fully engaged inside the cavity 17 so the stud 46 is fully retracted into said cavity. As a result the collimator is held on the carriage by the jaws. When the collimator comes to rest on the abutments 36 and 37 on being installed on the case, the tooth 11 may be retracted, thereby enabling the head 50 of the stud 46 to penetrate into the facing cavity 39 in the case 5. These two actions thus take place simultaneously such that unlocking the jaws 8 and 9 causes the collimator to be locked to the case 5. Once the studs such as 46 have entered the cavities such as 39, they have generator lines that bear, when the time comes, against the reaction plates 42 closing the tops of these cavities such as 39.

Under such conditions, the collimator is held on the case.

Instead of using longitudinal translation of elongate studs, it would be possible to design curved studs that are engaged in the case by rotation. For example, the tip 44 of the tooth 11 could give rise to such rotation by bearing against the edge of the base 45. It would also be possible to design studs that rest inside the cavities 39 of the case with the rear end of the teeth causing these other studs to emerge (e.g. by rotation) and engage in the facing cavities in the collimator simultaneously with the teeth being withdrawn from the cavities such as 11. To improve installation safety, the ends 50 of the studs bear against switches such as 51 once they have penetrated into the cavities 39, thereby operating a security or alarm system 52. The system 52 as shown constitutes a positive safety system: regardless of the fault that may arise, including a fault in the system 52 itself, an operating indicator lamp indicates that the system is safe.

As a complement to the abutments 37, the tooth 11 may include an adjustment screw 53 at its rear end for adjusting the position of its tooth vertically at the moment a locking or unlocking operation takes place on the gamma camera. These operations must be performed while the gamma camera is substantially horizontal. Similarly, the ground on which the carriage 1 runs may not be perfectly level, thus causing faulty presentation of the collimator to the case. To allow for this, the slides 24 and 25 are somewhat slack, making it possible for the collimator 2 to move a little about a hinge passing through the axis of the quarter turn handle 26. The tips 54 of the screws 53 then come into abutment against the tops of the reaction plates 42 so as to adjust the heights of the ends 44 of the teeth 11 so that said ends of said teeth can penetrate into the corresponding cavities 17. Under such conditions, the screws 53 are preferably disposed level with the middle teeth 11 and 14. In order to make it possible to have middle teeth in this way, it is preferable for there to be an odd number of teeth along each side. In order to facilitate engagement and also to limit play, the lateral studs 46 are preferably conical in shape.

We claim:

1. A system for installing a collimator on a detector of a gamma camera, the system comprising:
   a handling carriage,
   a collimator, and
   a gamma camera carried by a case wherein,
   the carriage comprises a frame provided with jaws for grasping the collimator;
   the collimator comprises a retractable stud, means for retracting the stud as the jaws grasp the collimator and means for extending the stud into a cavity in said case when the jaws release the collimator.

2. A system according to claim 1 wherein there are an even number of studs.

3. A system according to claim 1 wherein the stud is conically shaped.

4. A system according to claim 1 wherein the stud is retractable in translation.

5. A system according to claim 1 wherein the stud cooperates with electrical switches connected to a safety or alarm circuit.

6. A system according to claim 1 wherein the carriage includes a frame for holding the jaws, said frame includes means for displacing the jaws symmetrically relative to the frame.

7. A system according to claim 1 wherein the case has a tapering face for engaging a shield on the carriage so as to automate centering the collimator over the case.

8. A system according to claim 1 wherein the collimator includes pegs for fine centering of the collimator over the case.

9. A system for installing a collimator on a detector of a gamma camera, the system comprising:
 a handling carriage;
 a gamma camera case;
 a collimator which fits in said case and is attached to said case by a set of retractable studs which extend into cavities in said case when said collimator is disposed in said case; and
 said carriage comprises a means for grasping the collimator and simultaneously retracting said studs from the cavities in said case thereby releasing said collimator from said case.

* * * * *